United States Patent
Lechner (10) Patent No.: US 9,947,507 B2
(45) Date of Patent: Apr. 17, 2018

(54) METHOD FOR PREPARING CROSS-SECTIONS BY ION BEAM MILLING

(71) Applicant: Carl Zeiss Microscopy GmbH, Jena (DE)

(72) Inventor: Lorenz Lechner, Dublin, CA (US)

(73) Assignee: Carl Zeiss Microscopy GmbH, Jena (DE)

( * ) Notice: Subject to any disclaimer, the term of this patent is extended or adjusted under 35 U.S.C. 154(b) by 136 days.

(21) Appl. No.: 14/795,489

(22) Filed: Jul. 9, 2015

(65) Prior Publication Data

US 2017/0011885 A1 Jan. 12, 2017

(51) Int. Cl.
*G01N 1/32* (2006.01)
*H01J 37/302* (2006.01)
*H01J 37/305* (2006.01)

(52) U.S. Cl.
CPC ............ *H01J 37/3056* (2013.01); *G01N 1/32* (2013.01); *H01J 37/3026* (2013.01); *H01J 2237/31* (2013.01); *H01J 2237/3114* (2013.01); *H01J 2237/3151* (2013.01); *H01J 2237/31745* (2013.01); *H01J 2237/31749* (2013.01)

(58) Field of Classification Search
None
See application file for complete search history.

(56) References Cited

U.S. PATENT DOCUMENTS

| | | | |
|---|---|---|---|
| 6,527,967 B1 * | 3/2003 | Suzuki | G01N 1/32 216/62 |
| 7,427,753 B2 | 9/2008 | Pearl | |
| 2006/0037137 A1 * | 2/2006 | Song | A47D 13/063 5/99.1 |
| 2006/0071182 A1 * | 4/2006 | Sugiura | H01L 21/31105 250/492.21 |
| 2011/0108737 A1 * | 5/2011 | Pu | A61N 5/10 250/398 |

(Continued)

FOREIGN PATENT DOCUMENTS

| | | |
|---|---|---|
| EP | 2 840 588 | 2/2015 |
| JP | 04132909 A * | 5/1992 |

OTHER PUBLICATIONS

European Search Report for corresponding EP Appl. No. 16178177.8-1556, dated Nov. 18, 2016, 10 pages.

(Continued)

*Primary Examiner* — Wyatt Stoffa
*Assistant Examiner* — James Choi
(74) *Attorney, Agent, or Firm* — Fish & Richardson P.C.

(57) ABSTRACT

The disclosure provides a method for preparing a cross-section of a sample by milling with a focused ion beam. The cross-section is to be prepared at a pre-defined position. The method includes excavating a trench by milling in a first milling direction. The first milling direction leads away from the position of the cross-section to be prepared. The method also includes excavating the cross-section by enlarging the trench by milling in the reversed milling direction. The second milling direction leads towards the position of the cross-section to be prepared, whereupon the milling is completed at the position where the cross-section is to be cut. The desired largest milling depth is achieved at the completion of this milling step.

23 Claims, 8 Drawing Sheets

(56) References Cited

U.S. PATENT DOCUMENTS

| | | | | |
|---|---|---|---|---|
| 2013/0328246 A1* | 12/2013 | Wells | ............... | G01N 1/32 |
| | | | | 264/400 |
| 2014/0131315 A1* | 5/2014 | Salzer | ............... | B23K 26/03 |
| | | | | 216/94 |
| 2015/0048248 A1* | 2/2015 | Biberger | ............... | H01J 37/304 |
| | | | | 250/307 |

OTHER PUBLICATIONS

Tseng, "Recent Developments in Micromilling Using Focused Ion Beam Technology", Journal of Micromechanics and Microengineering, vol. 14, No. 4, p. R15-R34 (2004).

Wiggers de Vries et al., "Three-Dimensional Cathodoluminescence Imaging and Electron Backscatter Diffraction: Tools for Studying the Genetic Nature of Diamond Inclusions", Contributions to Mineralogy and Petrology, vol. 161, No. 4, p. 565-579 (2011).

Adams, D.P. Vasile, M.J. (2006): "Accurate focused ion beam sculpting of silicon using a variable pixel dwell time approach", *J. Vac. Sci. Technol B* 14(2), Mar./Apr. 2206, p. 836-844.

Bassim, Nabil; Scott, Keana; Giannuzzi, Lucille A.: "Recent advances in focused ion beam technology and applications", *MRS Bulletin*, vol. 39, Apr. 2014, p. 317-325.

* cited by examiner

METHOD FOR PREPARING CROSS-SECTIONS BY ION BEAM MILLING

FIELD

The present disclosure relates to methods and apparatuses for excavating trenches out of sample material by using ion beam milling.

BACKGROUND

Typical applications for focused ion beam (FIB) systems are the preparation of TEM lamellae, cross-sections, or samples suitable for 3D tomography. All these applications involve the excavation of a trench out of the sample bulk material.

Preferably, the cross-section or TEM lamella should be observable while being prepared. To that end, combined SEM-FIB-systems are used. Such systems include two particle-optical columns e.g. an electron column (SEM) and an ion column (e.g. a FIB column), whereby both columns are arranged in a particular angle to each other. This arrangement allows processing the sample by milling with the ion beam as well as observing the process via SEM.

A cross-section is a polished surface perpendicular to the sample surface. In order to create a cross-section of a given width and depth, a volume of sample material is removed by milling with the FIB. This will not only prepare the cross-section as such but also provide a viewing path for the SEM. Depending on the angle between SEM and FIB, the trench should feature a slope with the base of the slope at the bottom part of the cross-section. The sloped trench will allow the user to observe the entire cross-section. The desired angle of observation determines how much material has to be removed when preparing the sloped trench. The viewing angle does not always have to be the angle between the SEM column and the FIB column. Instead, sometimes steeper angles are chosen to reduce working distance (WD) or minimize material removal.

Similarly, TEM lamellae are prepared for lift-out by removing a volume of material from two opposing sides of the sample region of interest. This means that in principle two cross-sections have to be prepared, one at each side of the TEM lamella to be prepared. The amount of material to be removed depends on the desired shape of the lamella and the restrictions given by the accessible cutting angles for detaching the bottom of the lamella.

When excavating a trench out of the sample material, usually relatively large amounts of sample material have to be removed which is often a time-consuming procedure. Therefore, the feasibility of a particular investigation is often determined by whether the material removal can be accomplished within a reasonable time.

Thus, milling speed can be an important factor for the preparation of samples by ion beam milling.

Milling speed depends on a multitude of factors such as sample material, lattice orientation, ion current, ion species and/or milling geometry. Besides that, redeposition processes can play an important role. During milling, sample material is sputtered away from the sample, but a certain amount of the removed material is deposited onto the sample surface again. Often, redeposited material fills up most of the recently prepared trench, so that trenching speed is considerably reduced. Thus, the sputtering yield, i.e. the material removal rate, could be much higher with reduced or even without redeposition.

Usually, milling is done by processing individual milling objects. With the help of milling objects, which are geometrical patterns e.g. rectangles, the user can select the area to be scanned by the focused ion beam, thus defining the sample region to be milled. The milling objects are shown in the user interface of the machining system (FIB system or combined FIB-SEM-system), typically superimposed on a microscopic image of the sample surface.

The scanning strategy, i.e. the manner how the ion beam is guided over the sample region to be milled, has a strong impact on the achievable material removal rate. Currently, there are two established milling modes for coarse material removal: line milling and frame milling.

In line milling mode, a single line is scanned several times by scanning the ion beam forth and back along the line until the full ion dose for this region has been delivered. Then, the ion beam jumps to the next line, which is scanned in the same manner. Thus, the desired ion dose is delivered to each line in a single pass, which itself includes a plurality of forth and back passes along the same line. The milling is completed when the ion beam has scanned the last line of the respective milling object. With line milling mode relatively high removal rates are obtainable due to the edge geometry. Typically, the sputtering yield of line milling mode is six to eight times higher than that of frame milling mode. With line milling mode relatively deep trenches can be cut, creating a smooth cross-section at the lower end of the sloped trench. However, due to redeposition occurring in previously excavated regions of the trench, the observable area is limited by piled-up redeposition material. Thus, disadvantageous with line milling mode is, that it is difficult to generate a trench with a specific slope angle. Sometimes multiple line milling objects are superimposed and processed sequentially to remove redeposition and achieve the desired geometry.

In frame milling mode, the beam is scanned over the entire milling region in a first pass. As soon as a line has been scanned once, the ion beam jumps to the next line and so on until the frame is completed. When the frame is completed, which means that all lines of the frame have been scanned once, the beam jumps back to the first line of the frame and the process is repeated in a further pass. Therefore, during each pass only a small fraction of the total ion dose is applied to the sample material. The milling process is completed when the desired total ion does has been applied.

When using frame milling mode to prepare a trench for cross-sectioning, usually several milling objects are superimposed to approximate the desired trench slope. This leads to a staircase form (staircase milling). Since each milling object is scanned several times during exposure, in each pass redeposition from the previous pass is removed. However, because of the short dwell time for each beam position on the sample, sputtering yield is remarkably lower than for line milling. Moreover, redeposition—despite not being visible—reduces the effective sputtering rate as the aspect ratio increases.

However, the distinction between frame milling and line milling is by convention. Very slow frame scan (long dwell time) or very narrow line spacing (smaller than the beam diameter) makes frame mode and line mode similar.

Overall, neither the known procedures for line milling mode nor those for staircase milling make optimal use of the applied ion dose.

It is known in the art to use a combination of coarse milling and fine milling, i.e. different milling currents, in order to prepare a cross-section. Initially, a high current is used to remove an amount of material. Then, a significantly lower current is applied for cleaning or polishing the cuts while employing a smaller beam diameter (i.e. a finer probe).

By way of example, in U.S. Pat. No. 7,427,753, a sequence of coarse scanning and fine scanning is suggested using a line-interlace mode by creating sub-groups of milling lines.

Moreover, Adams, D. P; Vasile, M. J. (2006): *J. Vac. Sci. Technol B* 14(2), March/April 2206, p 836-844 and Bassim, Nabil; Scott, Keana; Giannuzzi, Lucille A.: *MRS Bulletin*, Vol 39, April 2014, p. 317-325 suggest using a boustrophedonic frame scanning mode, wherein the pixel dwell time is varied (Adams & Vasile (2006)).

Another strategy to accelerate milling speed is to increase the milling current, i.e. the beam current used for milling. This can be done for example by using a plasma FIB. However, increasing the milling current also increases the beam (i.e. probe) diameter, leading to a decrease of accuracy.

SUMMARY

The present disclosure proposes a milling technique for line milling mode that addresses redeposition without sacrificing speed by exploiting the angle dependent sputtering effect. Milling is the removal of sample material due to the impact of a beam of ions, preferably a focused beam on ions, on the sample surface.

In one general aspect, the disclosure provides a method for preparing a cross-section of a sample by milling with an ion beam, wherein the cross-section is to be prepared at a pre-defined position (ROI). The method includes excavating a trench by milling in a first milling direction. The first milling direction leads away from the position of the cross-section to be prepared (ROI). The method also includes excavating the cross-section by enlarging the trench by milling in the reversed milling direction. This second milling direction leads towards the position of the cross-section to be prepared (ROI), whereupon the milling is completed at the pre-defined position where the cross-section is to be cut. The desired largest milling depth is achieved at the completion of this milling step.

The method can include the additional step that before excavating the trench, an initial trench is excavated by milling in the second milling direction leading towards the position of the cross-section to be prepared (ROI).

During the excavation of the cross-section an ion dose can be applied which is increasing with the decreasing distance of the ion beam from the position of the cross-section to be prepared (ROI).

During excavating the trench an ion dose can be applied that is different from the ion dose applied during excavating the initial trench.

The excavation of the initial trench can be performed by applying a first ion dose, the first ion dose being suitable for coarse removal of sample material. The excavation of the trench can be performed by applying a second ion dose, the second ion dose being suitable for removal of redeposited material. The excavation of the cross-section can be performed by applying an increasing ion dose until the full ion dose required for the desired depth of the cross-section is applied when completing the milling of the cross-section. The first ion dose can be higher than the second ion dose. The dose ratio between the first ion dose, the second ion dose and the full ion dose can be described by $\frac{1}{2} :: \frac{1}{3} :: 1$.

Excavating the trench can be performed by milling a first region of the sample and excavating the cross-section is performed by milling a second region of the sample. Both regions can be defined by their sizes, positions and geometrical shapes, wherein the first region and the second region differ in size and/or position. The first region can be located in a distance from the position of the cross-section to be prepared (ROI). The first region can be overlapping with the second region.

Excavating the trench can be performed by milling a first region of the sample. Excavating the cross-section can be performed by milling a second region of the sample. Excavating the initial trench can be performed by milling a third region of the sample. All regions can be defined by their sizes, positions and geometrical shapes, wherein the first and the third region differ in size and/or position. The first region can be overlapping with the third region. The first region can be larger than the third region. The third region can be located in a distance from the position of the cross-section to be prepared (ROI).

The geometrical shape of the regions to be milled can feature a taper in width in order to counteract sidewall redeposition. The geometrical shape can be a trapezoid.

In at least one step of the method, excavating can be facilitated by gas assisted etching.

In another general aspect, the disclosure provides a particle-optical apparatus including a FIB system configured to perform a method disclosed herein.

In a further general aspect, the disclosure provides a computer program product that includes a sequence of commands, which, when executed by a controller unit, makes a FIB system perform at least a method disclosed herein.

In principle, according to the present disclosure a trench for the preparation of a cross-section is excavated by performing different milling steps, wherein the milling direction is reversed in the subsequent milling steps. The milling direction is the overall sense of moving the ion beam relative to the sample area to be processed.

This is different to the known boustrophedonic frame milling. When performing boustrophedonic frame milling, the beam direction of every other scanned line is reversed, so that the beam is moved within a frame in an ox-turning-like milling manner. However, in the present disclosure the change of the milling direction refers to milling steps related to milled boxes (i.e. sample areas), not to the scanning of individual lines. In fact, the term "milling direction" refers to the sequence of execution of the line-shaped milling steps that combined together constitute the milling object.

Changing the direction of milling is substantial for the present disclosure. In line milling, the ion beam is line-wise scanned across the sample surface within the limits of a milling object. A milling object, for example a rectangle, is two-dimensional so that it shows an expansion in x-direction as well as one in y-direction, both directions being perpendicular to each other. The lines to be scanned extend in x-direction. The ion beam is scanned quickly back and forth in x-direction along a first line. After the desired ion dose has been applied to the first line, the ion beam moves on to a second line. Usually, the second line is in y-direction adjacent to the first line. Typically, the positions of the beam spots of the second line partially overlap with the beam spot positions of the first line. In such a manner, the ion beam is unidirectionally moved from line to line in y-direction until the last line of the milling object has been scanned. This is called movement in milling direction. In contrast to the quick motion in x-direction, the ion beam performs a relatively slow movement in y-direction. Thus, milling is in principle performed by executing a series of partially overlapping line mills.

Typically, the face of the cross-section is one of the side walls of the milled trench. Therefore, it is reasonable to define the milling direction in relationship to the region of interest (ROI), i.e. the position where the cross-section is to be cut. The ion beam movement in y-direction can be towards the ROI. This is also called forward milling or milling in forward direction. On the other hand, the ion beam can be moved in the opposite direction, i.e. leading away from the ROI. This is called backward milling or milling in backward direction.

According to the present disclosure, an initial trench is excavated by milling forward, i.e. towards the intended position of the cross-section. When doing so, redeposition occurs unavoidably so that the initial trench is at least partly filled again with redeposition material.

In a next step, the initial trench is milled again, thus enlarging the trench and removing the redeposited material from side walls and bottom of the trench. Compared to the previous milling step, the milling direction is reversed, thus leading away from the ROI (backward milling).

Finally, a cross-section as such is excavated in another milling step. The cross-section is cut by milling in forward direction. Milling is completed, when—more or less—the exact position of the cross-section is reached. This means that the forward milling ends at the face of the cross-section so that a smooth cut is created. The desired largest milling depth should be obtained at the end of this milling step. This ensures that the cross-section is excavated with the desired depth.

The present disclosure is based on the finding that a dynamic change of the ion incidence angle leads to a higher material removal rate. During line milling, the material removal creates a slope on which the ions impact at a steeper angle. Moreover, sputtered material is mainly redeposited at regions that have been machined before. This will lead to a change in sample topography. Since material sputtering yield strongly depends on the ion incidence angle, it increases up to eight fold when this angle changes from perpendicular to 85°. Due to the reversal of the milling directions according to the present disclosure, all milling steps are performed up the slope of the redeposited material. Thus, sputtering yield can be maximized, because uphill milling (i.e. up the slope) dramatically increases sputtering yield in line milling mode, in particular at long dwell times.

In a further embodiment of the disclosure, excavating an initial trench is omitted, because this milling step is not compulsory. For this embodiment, the method starts with backward milling the actual trench.

With the embodiments mentioned above, it is also possible to apply different ion doses to the sample surface and/or mill sample regions of different sizes when executing the different milling steps.

BRIEF DESCRIPTION OF THE DRAWINGS

Exemplary embodiments are explained below with the help of the drawings, in which.

DETAILED DESCRIPTION

Figure 1:
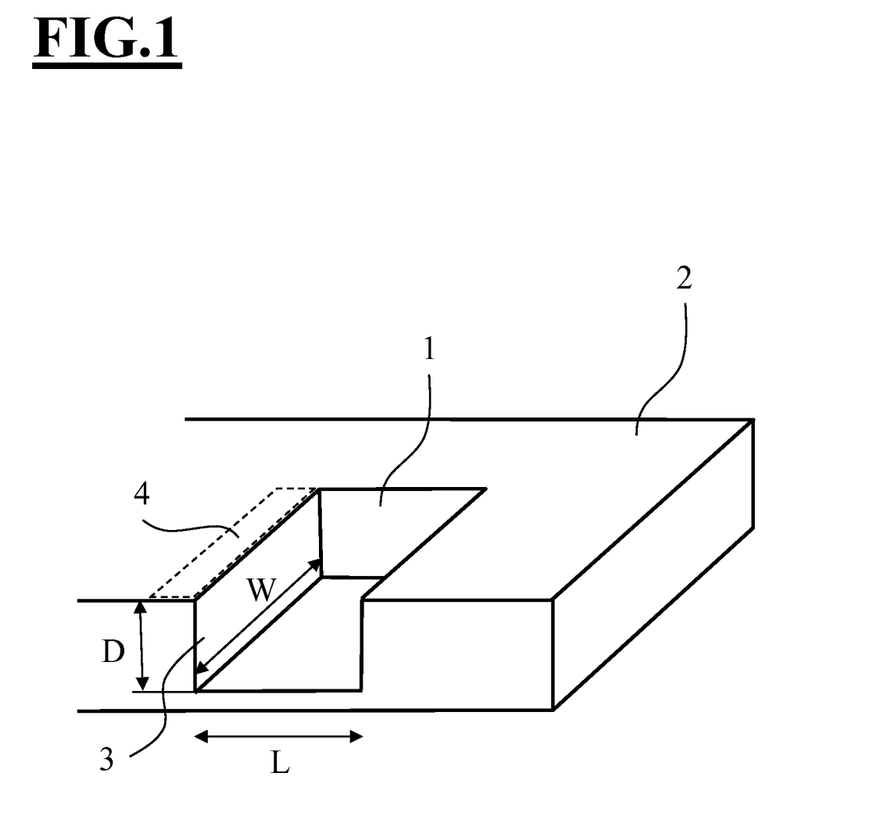
FIG. 1 shows a cross-section that has been prepared by excavating a trench out of sample bulk material.

FIG. 1 depicts a cross-section 3, which has been prepared by milling a trench 1 into the bulk material of the sample 2. A cross-section is a vertical sample surface preparation, that is usually more or less perpendicular to the surface of the sample. The cross-section 3 is located at a region of interest (ROI) 4. The trench 1 shows certain width W, length L and depth D. Trench 1 and cross-section 3 have the same width W and depth D, because one side wall of the trench 1 is the face of the cross-section 3.

Figure 2:
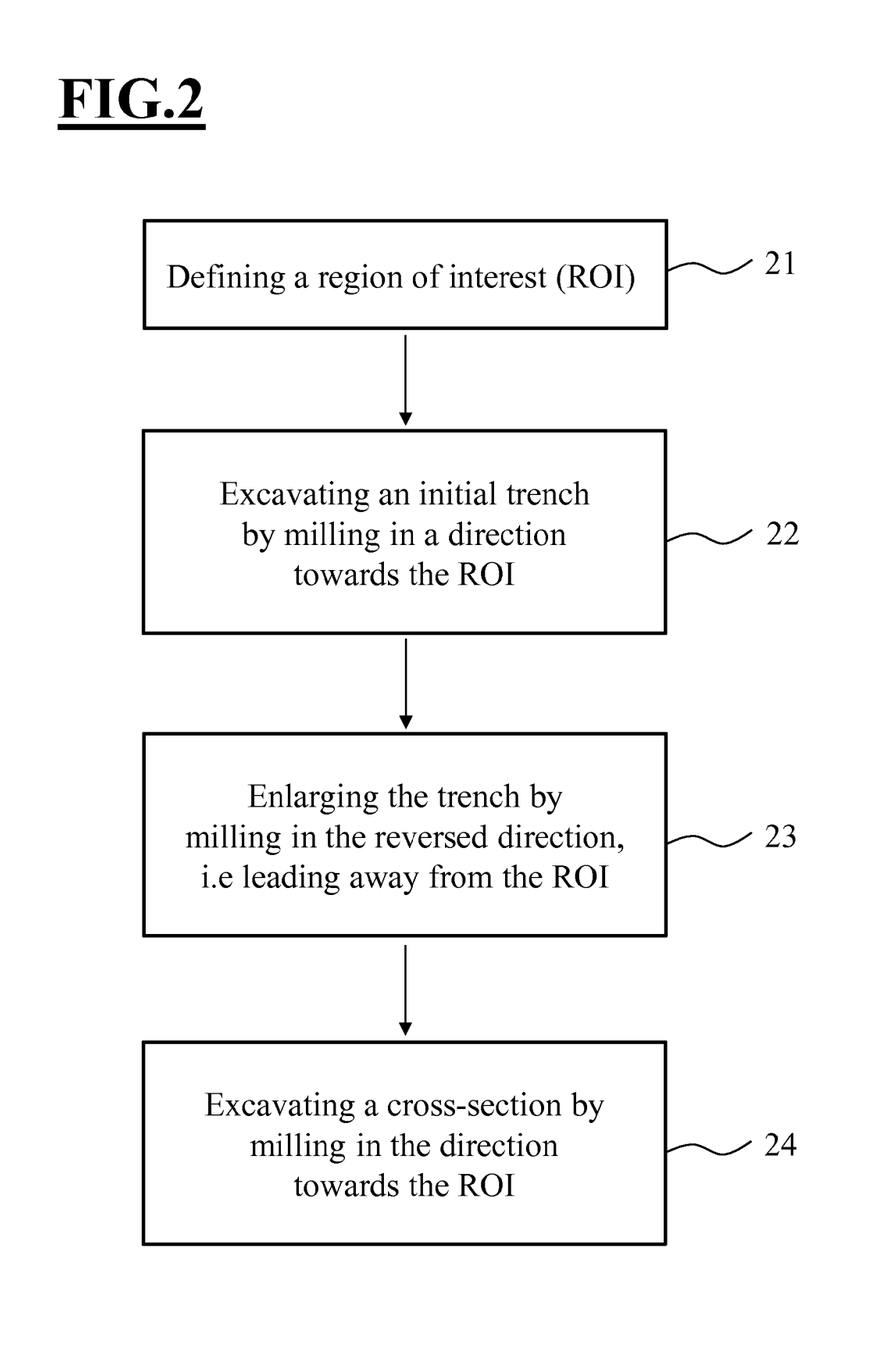
FIG. 2 is a flow-chart of an embodiment of the disclosure.

FIG. 2 shows a flow-chart of a first embodiment of the present disclosure, wherein a cross-section is prepared by milling with a focused ion beam. In a first step 21, a region of interest (ROI) is selected and defined by the user. The user selects the region on the sample where the cross-section should be cut from. Typically, the user determines size and position of the ROI with the help of a SEM- or FIB-image of the sample, wherein a milling object can be superimposed. Position, size and geometrical shape of the milling object correspond to position, size and geometrical shape of the respective sample region to be machined.

Milling objects (sometimes also called milling boxes) are geometrical patterns for example a line, a rectangle, a trapezium or any other geometrical shape, depending on the desired preparation. In addition, a milling object is characterized by several milling parameters such as milling mode and milling current. Likewise, other distinguishing features are: position, width and height of the excavation to be milled. Since the depth of a trench depends on material and milling strategy (thus involving a calibration step), usually the ion dose to obtain a desired depth is another parameter assigned to a milling object.

In order to execute the method of the disclosure the user can define several milling objects, i.e. can define several sample regions to be machined.

In step 22, an initial trench is excavated by milling. This is done by forward milling, i.e. a sample region is scanned by the focused ion beam in a direction towards the predefined ROI. Milling should be performed in line milling mode, because line milling has the advantage, that a relatively high sputtering yield can be obtained due to the edge effect.

In step 23, the trench is being enlarged. This is done by milling in the reversed direction i.e. now leading away from the ROI. Doing so, sputtered material, that has been redeposited in the previous milling step, is removed.

Finally, a cross-section is excavated by milling in forward direction in step 24. The milling stops when the focused ion beam has milled a line that is located at the intended position of the cross-section to be cut. This means that the last cut side wall of the trench becomes the face of the cross-section. Consequently, the region excavated in step 24 has to be milled in a way that a width and a depth are excavated that match with the desired width and depth of the cross-section. Therefore, the desired maximum milling depth should be achieved at the completion of step 24. This means, that during this milling step the excavation depth should be increased so that a sloped trench is cut. Alternatively, milling of step 24 can stop before reaching the intended position of the cross-section in order to allow for polishing under low current conditions (fine polishing).

The significant difference in sputtering yield between line milling mode and frame milling mode results from the dynamic change of the incidence angle. During milling in line milling mode, the material removal creates a slope on which the ions impact at a steeper angle. This change in local topography then increases the sputtering yield. For this effect to happen, the beam has to modify the surface significantly during the milling process, i.e. during the pixel dwell time or line dwell time.

In experiments performed by the inventor, the suggested milling mode was consistently faster than other milling modes, e.g. it was found that the method according to the disclosure enabled up to 3.5 times speed gain compared to staircase milling (i.e. frame milling). This speed improvement is a result of the increased angle-dependent sputtering yield and can be realized for any common milling depth. In contrast to multi-pass milling, the speed gain is also the case for high-current milling.

Since the sputtering yield is material specific, it is desirable to determine material specific milling rates for each material. This can be easily done by milling a box in frame mode to a depth specified for a reference material e.g. silicon (Si). Then, a line pattern, e.g. a horizontal line or two crossed lines, is milled over the excavated box. When observing the milled box with the superimposed line pattern cut under a certain angle, the depth can be measured with the help of a measuring function provided in the particle-optical instrument. The observation angle is either obtained by tilting the sample, by way of example when observing the sample with a single beam instrument, or—when using a combined system—due to the fact, that FIB-column and SEM-column are arranged under a certain angle. The milling rate is then calculated based on dose versus depth. The milling rate for the proposed method is obtained by multiplying the measured frame milling rate by a constant factor.

Figure 3:
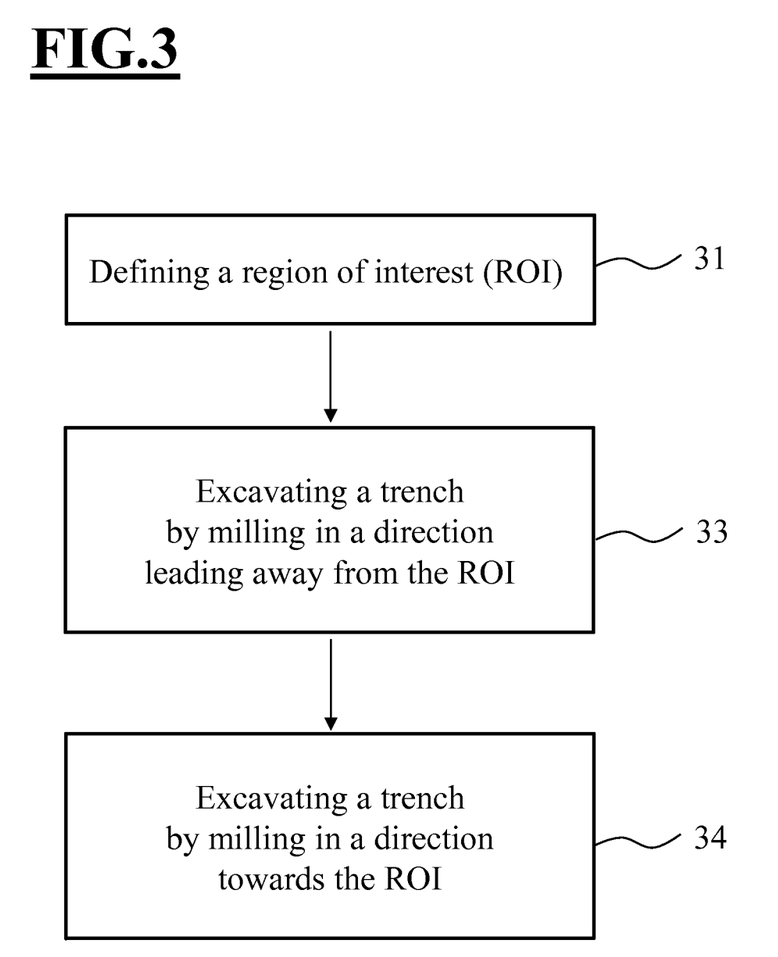
FIG. 3 is a flow-chart of a second embodiment of the disclosure.

FIG. 3 shows a flow-chart of a further embodiment of the present disclosure, which is similar to the first embodiment. However, compared to the first embodiment, the excavation of an initial trench is omitted.

The method according to this embodiment includes step 31, wherein a ROI is selected as described for FIG. 2. Then a trench is excavated by milling in backward direction (step 33).

Finally, the cross-section is excavated (step 34) by milling in forward direction. Summarizing, this embodiment includes two milling steps with opposite milling directions, being started with backward milling. This embodiment might be advantageous when working with gas assisted etching, because with this technique higher sputtering yields and lower redeposition rates can be obtained. With gas assisted etching, the milling process is supported by an etching gas introduced to the sample surface. Due to the reaction of the gas with the sample material (i.e. etching) the material removal rate can be increased. When the reaction between gas and sample material leads to the formation of volatile compounds, moreover redeposition will be reduced.

This means that in the method according to this embodiment of the disclosure, at least one of the steps including excavating can be facilitated by gas assisted etching so that the primary excavation of an initial trench as shown in FIG. 2 might not be involved.

Figure 4:
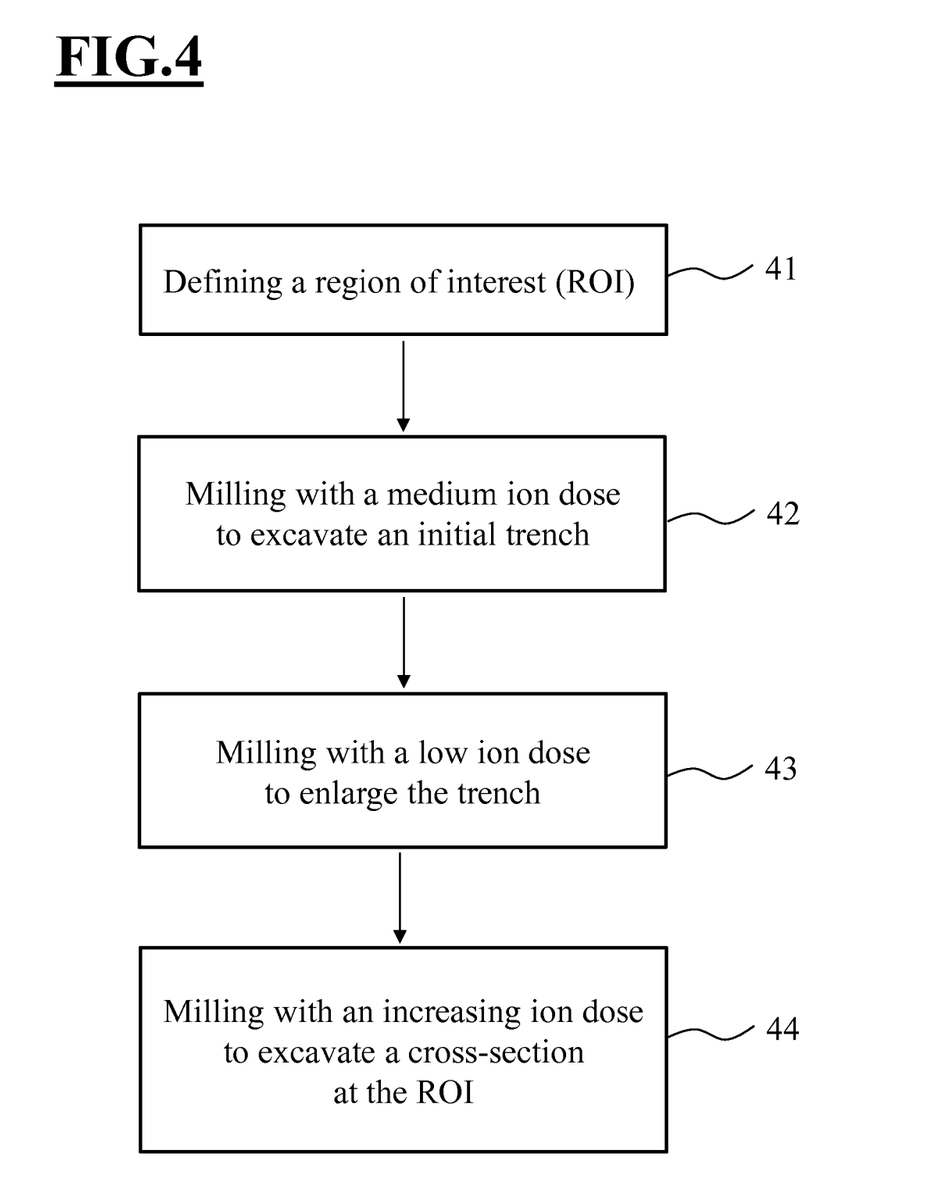
FIG. 4 is a flow-chart of a third embodiment of the disclosure.

FIG. 4 shows a flow-chart of another embodiment of the disclosure, wherein the ion doses applied to the beam spots, i.e. the spots on the sample surface, where the ion beam impinges, vary between the different milling steps. The term "ion dose" is understood as the product of beam current and time per area, typically indicated as $nC/\mu m^2$ or $ions/\mu m^2$.

The embodiment shown in FIG. 4 is similar to that described in FIG. 2. As described for FIG. 2, a region of interest (ROI) is selected by the user (step 41). Then, an initial trench is excavated (step 42). This is done by milling in forward direction with a first ion dose, that is suitable for coarse removal of sample material.

Generally speaking, the ion dose for excavating a trench with a certain depth has to be selected depending on the sample material and the desired depth. Therefore, suitable ion doses have to be found for every individual application and can vary in a wide range. However, for a given material and ion current density there is a minimum ion dose, i.e. a minimum milling depth that is applied for the described procedure to work.

The first ion dose should be a medium dose when compared to the ion doses applied during the following milling steps. Applying a medium ion dose has the effect, that sample material is coarsely removed.

In step 43, the trench is enlarged by applying a second ion dose that is suitable to remove the redeposited material. Moreover the trench can be enlarged in this step. Typically, the second ion dose differs from the first ion dose. More specific, the first ion dose often is higher than the second ion dose. Therefore, the second ion dose can be considered as low dose compared to the other ion doses applied when performing the method of the present disclosure. The region milled in step 43 can be different compared to that one milled in step 42.

Finally, in the next milling step 44 milling is done with an increasing ion dose, so that a sloped trench is excavated and one sidewall of the trench becomes the cross-section located at the pre-defined ROI. As described for FIG. 2, the milling process stops when the focused ion beam has milled a line that is located at the exact position of the cross-section. However, it is also possible to stop the milling ahead of the exact ROI location, e.g. to allow for low current polishing to remove curtaining or other high current milling artifacts.

For excavating a desired depth out of sample material, a certain ion dose, which is dependent on the sample material, has to be applied. In order to obtain a sloped trench with a pre-defined depth, the ion dose is increased during milling until the full dose for excavating the desired depth is applied at the completion of this milling step. This ensures that the full depth is excavated at the cross-section. In other words: during the excavation of the cross-section an ion dose is applied that is increasing while the distance of the ion beam from the cross-section is decreasing. This means that the lowest ion dose is applied at a sample region distant from the ROI and the highest ion dose is applied at a sample region near the ROI.

Summarizing, a cross-section can be prepared by performing different milling steps, wherein
the excavation of the initial trench is performed by applying a first ion dose, the first ion dose being suitable for coarse removal of sample material; the excavation of the trench is performed by applying a second ion dose, the second ion dose being suitable for removal of redeposited material; and the excavation of the cross-section is performed by applying an increasing ion dose until the full ion dose for the desired depth of the cross-section is applied when completing the milling of the cross-section.

It has been shown to be advantageous, when the ratio of [first ion dose:second ion dose:full ion dose] can be described as [medium:low:full]. In an exemplary embodiment, this ratio can be [½::⅓:1], meaning that the initial trench is milled with half of the full ion dose to excavate the desired maximum depth of the excavation, while the trench is milled with a third of the full ion dose to excavate the desired maximum depth. However, the disclosure is not restricted to this ratio, but can also be performed with other suitable ratios depending on the specific application.

Figure 5:
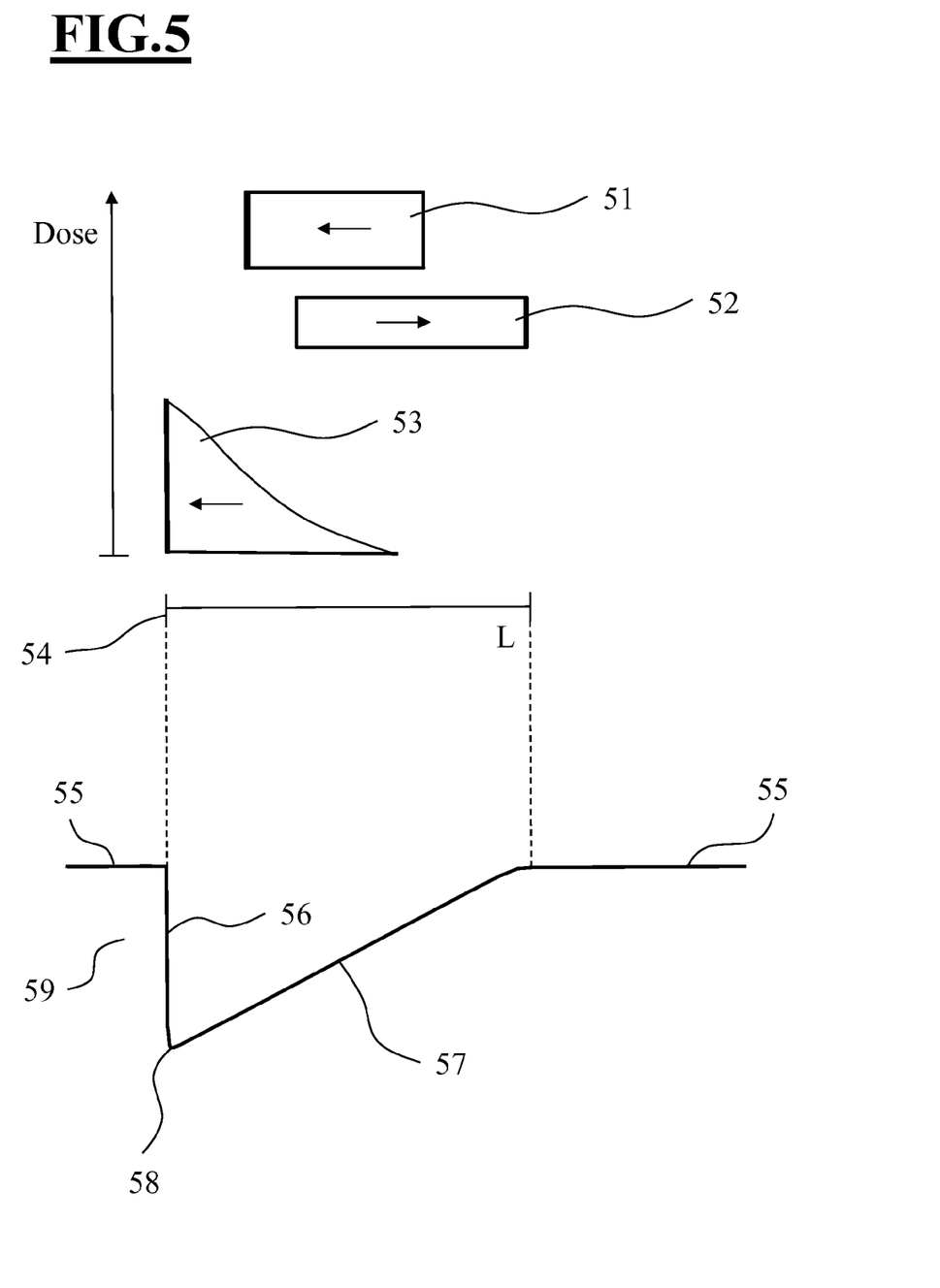
FIG. 5 shows schematically selected features of milling steps according to an embodiment of the disclosure.

FIG. 5 shows schematically selected features of the different milling steps of an embodiment of the disclosure. In the upper part of the figure, the applied ion dose (ordinate) is outlined versus the length L (abscissa) of the machined sample regions. The position of the ROI 54 along the length-axis is tagged on the abscissa L.

The boxes 51, 52 and 53 represent the different milling steps. In the direction of the abscissa the boxes 51, 52, 53 represent length and spatial distribution of the sample regions to be milled, wherein the arrows show the milling direction in relation to the ROI 54. However, the width of the regions to be milled is not shown in this type of illustration. Instead, in the direction of the ordinate, the boxes 51, 52, 53 show the applied ion dose.

In the first step 51, a medium ion dose is applied to a first sample region in order to excavate an initial trench. This is done while milling forward, i.e. milling towards the ROI 54.

Then, a low ion dose is applied in a further milling step 52 for enlarging the excavation. The region to be milled can be shifted along the length axis. This means that the milling process during step 52 can start in the middle of the previously excavated trench. Moreover, the region milled in step 52 can extend beyond the size of the region milled in step 51. The region milled in step 52 can extend to the maximum total length of the excavation.

In step 53 a cross-section is excavated. This is done by milling forward until the ROI is reached or is almost reached. If the cross-section should be prepared by a final fine polishing step it is advantageous to stop milling before the ROI is reached, so that a thin layer of material still covers the intended cross-section.

The ion dose is increased while milling, so that the depth of the excavated trench is increasing. The milling can start in the middle of the previously excavated trench by applying a low ion dose. Then, the ion dose is increased until the full ion dose is reached that for milling the desired depth of the cross-section. More precisely, during the excavation of the cross-section an ion dose is applied that is increasing while the distance of the ion beam from the cross-section is decreasing. This means that the lowest ion dose is applied at a sample region distant from the ROI and the highest ion dose is applied at a sample region near the ROI.

In the lower part of FIG. 5 a side view of the profile of the excavation is depicted. An excavation 56, 57, 58 has been cut out of the sample bulk material 59. The excavation includes a cross-section 56 and a sloped trench 57 with an area of maximum depth 58. The position of the cross-section 56 corresponds to the position of the ROI 54, tagged in the upper part of FIG. 5. In a distance from the excavation 56, 57, 58 the original surface 55 of the sample is maintained.

Figure 6:
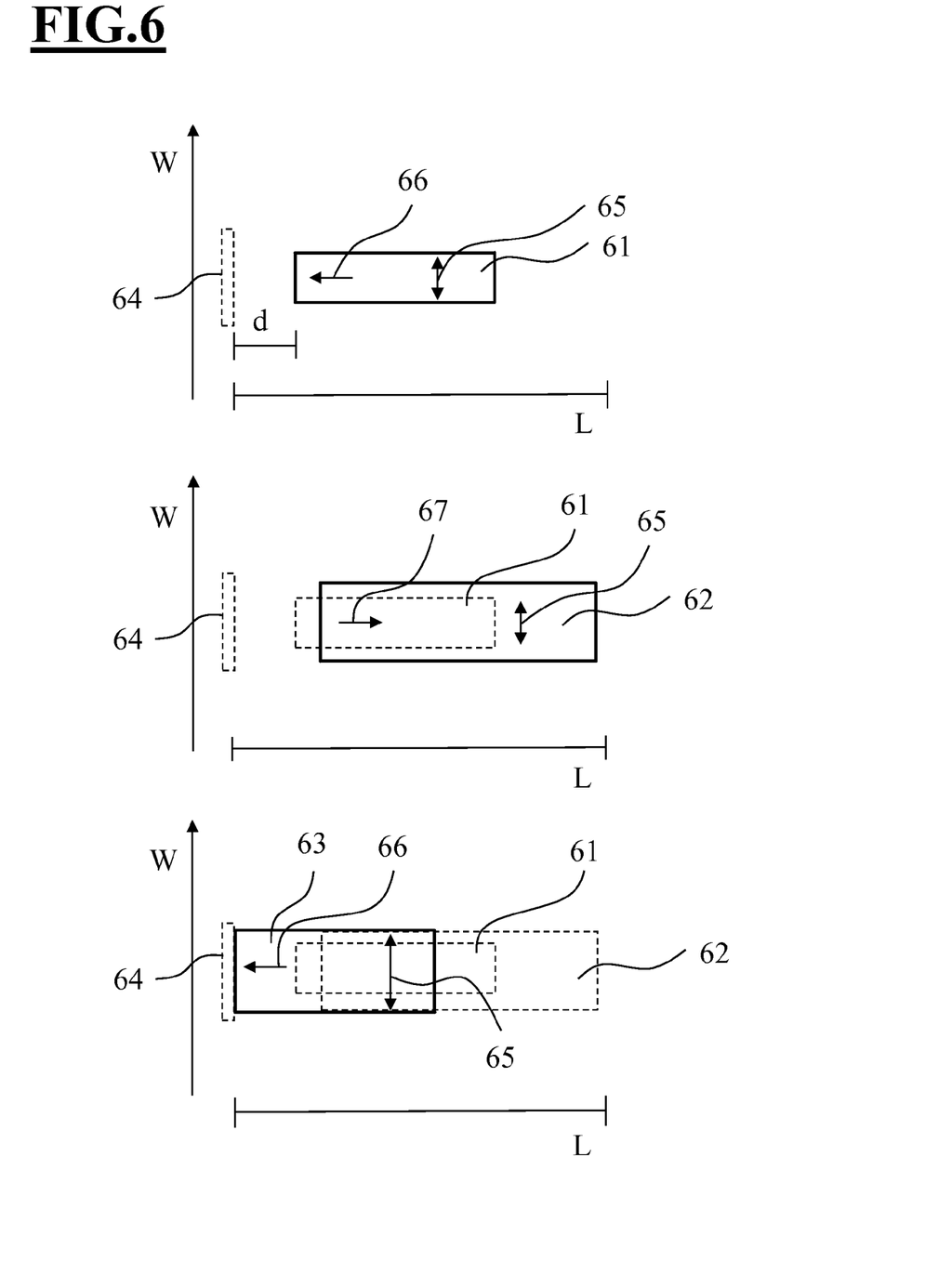
FIG. 6 shows the layout of the milled sample regions for another embodiment.

FIG. 6 shows the layout of milled sample regions 61, 62, 63 for another embodiment of the disclosure. The sample regions 61, 62, 63 to be milled can be specified by defining milling objects. In this case, the layout of the milling objects is the same as the layout of the sample regions to be milled, as shown.

The coordinate system represents the two-dimensional layout of the sample regions. The ordinate shows the width W of the regions 61, 62, 63, while the abscissa shows the length L of the regions 61, 62, 63. The definition of length L and width W correspond to the definition given for FIG. 1. The position of the ROI 64 is indicated.

To perform the milling, the focused ion beam is moved quickly forth and back along multiple lines, as indicated by a double arrow 65, representing the scanning direction. The scanned lines 65 can be parallel to the width W of the sample region 61, 62, 63.

The milling directions 66, 67 extend along the length L of the sample region 61, 62, 63, either being forward milling 66 (towards the ROI) or backward milling 67 (leading away from the ROI).

In the upper part of FIG. 6, a region to be milled 61 (in this case a rectangle) is shown. Excavation of region 61 by milling with the focused ion beam creates an initial trench. Region 61 may be positioned in a distance (d) from the ROI 64, so that the area adjacent the ROI is not machined (i.e. milled) when milling the initial trench.

In the center, FIG. 6 shows another region 62 to be milled. When milling region 62, a trench is created. Region 62 can be larger than region 61, if the trench should be larger than the initial trench. Moreover, region 62 can be shifted along the length-axis compared to region 61. This means that region 61 and region 62 can differ in size and/or position. Moreover, region 62 can be overlapping with region 61, so that sample material that has been redeposited while milling the initial trench is removed when excavating the trench.

In the lower part of FIG. 6, milling region 63 for excavating the cross-section as such is shown. The region 63 can differ from region 62 in size and/or position. For example, region 63 can be shifted along the length-axis, so that the positions of region 62 and region 63 are different. It is also possible that the size of region 63 is different from that of region 62, e.g. because region 63 is larger than region 62 so that the largest excavation is milled at the end of the milling process.

On the other hand, it is advantageous to apply an ion dose to milling region 63 which is increasing with the decreasing distance of the ion beam from the ROI. This means that during the excavation of the cross-section an ion dose is applied that is increasing while the distance of the ion beam from the cross-section is decreasing. Thus the lowest ion dose is applied at a sample region distant from the ROI, while the highest ion dose is applied at a sample region near the ROI. Advantageously, milling region 62 is overlapping with milling region 61 and/or milling region 63.

Figure 7:
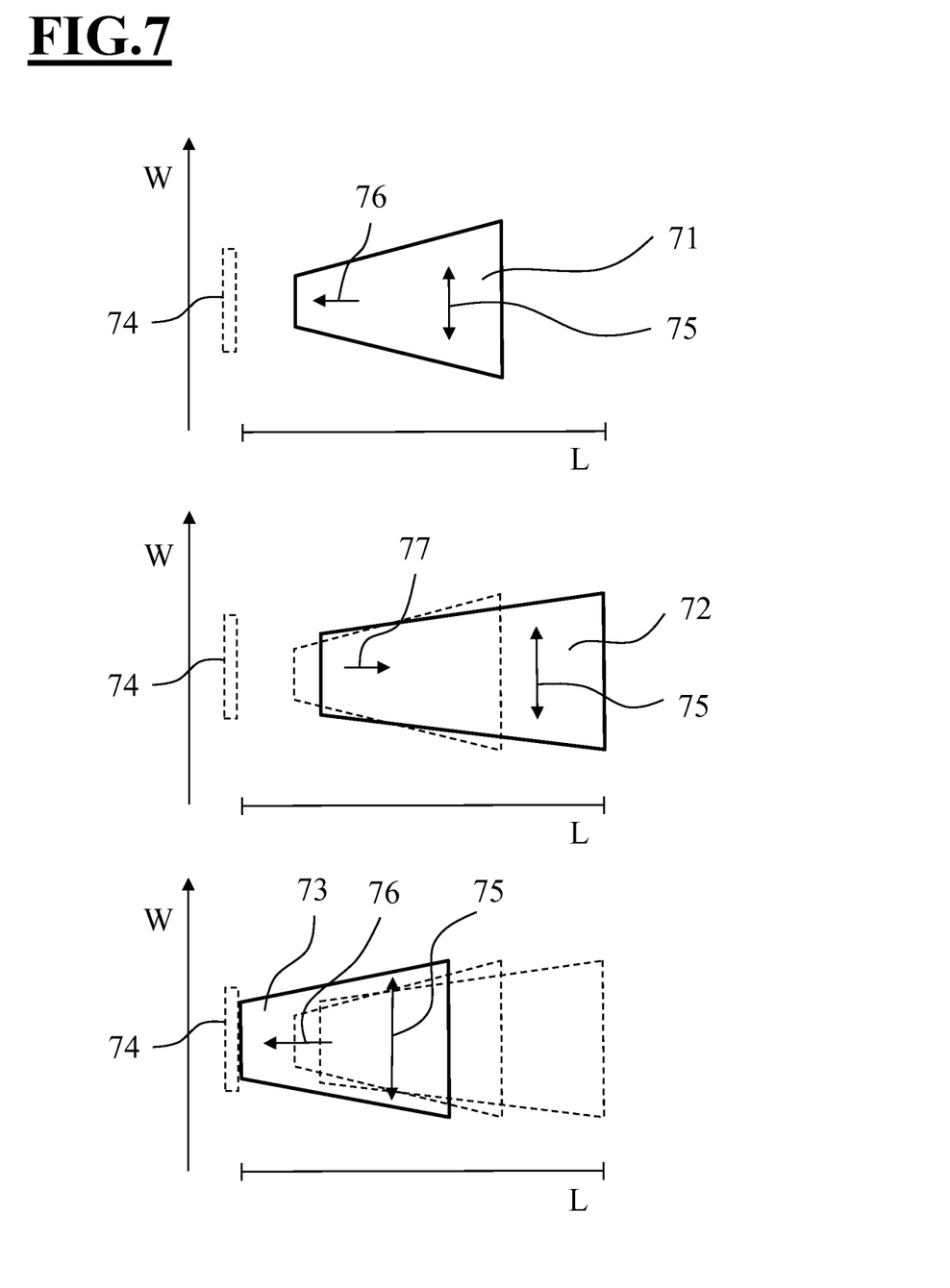
FIG. 7 shows the layout of the milled sample regions for another embodiment.

FIG. 7 shows another exemplary layout of milled sample regions. The layout is very similar to that shown in FIG. 6, but the shape of the milled regions is tapered. The tapered shape can be—for example—a trapezoid, which is a flat shape with four straight sides, wherein one pair of opposite sides are parallel and the other pair are not parallel. The shape tapered in width is beneficial, because it can counteract redeposition at the sidewalls of the trench.

In the upper part of FIG. 7 a milling region 71 with the shape of a trapezoid is shown, the milling of which will create an initial trench. In the center, FIG. 7 shows another milling region 72 for the creation of a trench. Region 71 and region 72 can differ in size and/or position.

Milling region 73 for excavating the cross-section as such is shown in the lower part of FIG. 7.

Again, region 73 can differ from region 72 in size and/or position as described for the similar layout of FIG. 6. Milling regions 71, 72, 73 can be overlapping each other as described for milling regions 61, 62 and 63 in FIG. 6.

In another advantageous embodiment, at least near the ROI 74 the width of the first milling region 72 can be larger than the width of the third milling region 71, resulting in the trench being larger than the initial trench near the ROI.

Figure 8:
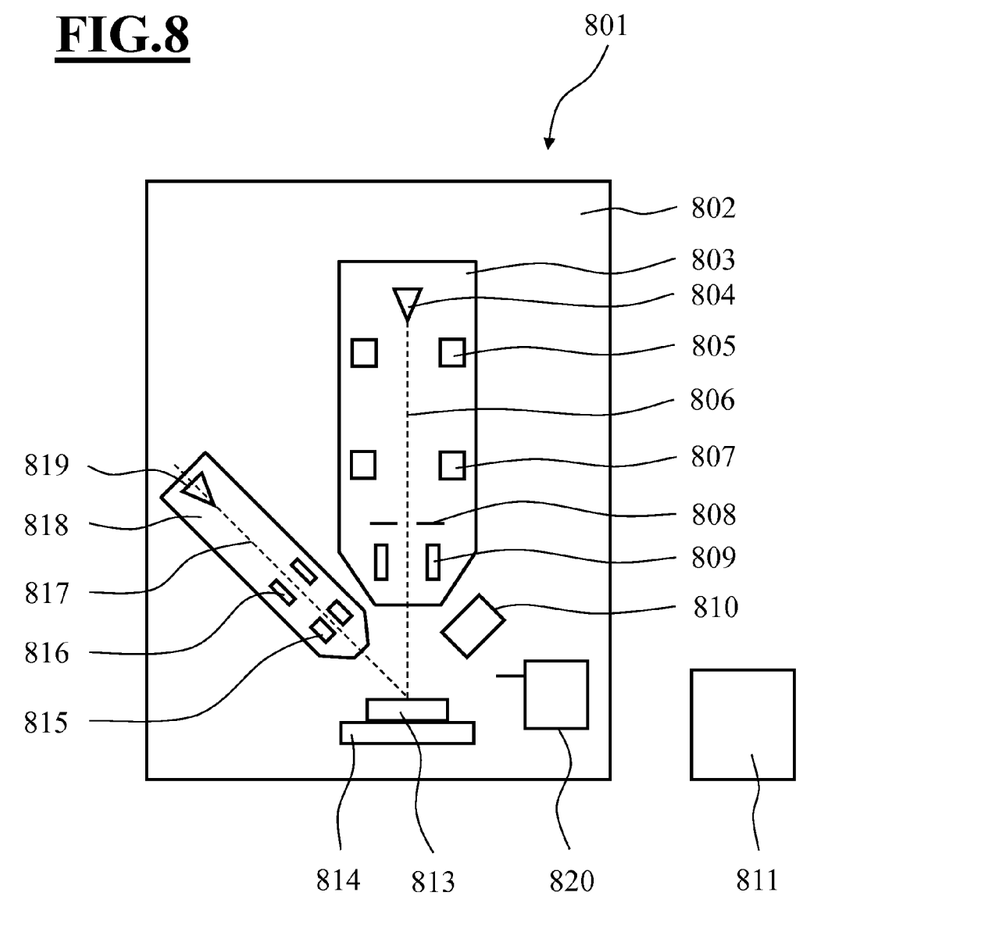
FIG. 8 shows a schematic of a particle-optical instrument configured to perform the method of the present disclosure.

FIG. 8 shows schematically a particle-optical apparatus 801 including a FIB system, which can be used to carry out the method of the disclosure. More precise, FIG. 8 shows a combined FIB-SEM-system. Alternatively, it is also possible to execute the method of the disclosure with a sole FIB system.

The particle-optical apparatus 801 includes an electron-optical column 803 as well as an ion-optical column 818. In the electron-optical column 803, an electron source 804 is configured to produce electrons. In operation, these primary electrons are accelerated along the optical axis 806 of the electron-optical column 803, focused by a first lens system 805 and a second lens system 807 and cut by at least one aperture 808. Moreover, the electron-optical column 803 includes a deflection system 809 allowing to scan the electron beam over the sample 813.

The sample 813 is located in a sample chamber 802, which can be maintained under vacuum conditions. The particle-optical apparatus 801 includes a movable sample holder 814 for holding the sample 813. When primary electrons impinge on the sample 813, interaction products are emitted from the sample 813 which can be detected by a detector 810 in order to generate a microscopic image of the sample 813.

The particle-optical apparatus 801 also includes an ion-optical column 818 with an ion source 819, a deflection system 816, and a focusing lens 815. The ion source 819 is configured to emit ions, e.g. Galium (Ga) ions or Helium (He) ions. In operation, the emitted ions are accelerated along the optical axis 817 of the ion-optical column 818, wherein the ion beam is bundled, so that a focused beam of ions can be scanned in a defined matter over the sample 813. The focused ion beam impinging on the sample surface can be used to sputter material from the sample 813, a process that is also called milling.

Optionally, the particle-optical apparatus 801 may include a gas injection mechanism 820 including a needle for introducing gas into the sample chamber 802. Advantageously, the gas injection mechanism 820 includes a reservoir for providing a gas suitable for etching dependent on the specific application.

Moreover, the particle-optical apparatus 801 includes a controller unit 811, which is configured to control the operation of the particle-optical apparatus 801.

The method according the disclosure enables full dose-optimized automation of cross-sectioning and TEM-sample preparation. By making angle-enhanced sputtering predictable, it allows algorithmic determination of optimum milling patterns which was previously only possible for staircase milling. The suggested method ensures that relative milling rates remain high, independent of milling probe size.

For the microscope user intending to prepare a cross-section, only three parameters are used to define the cross-section: position, width and depth. Knowing the sample material, all other milling and geometry parameters can be deducted. Based solely on such parameters, implementation of the method according to the present disclosure, allows one to automatically generate and execute an optimized sample preparation routine.

This implementation can be realized for instance by a computer program product, including a sequence of commands, which—when executed by the controller unit 811—makes the FIB system perform at least a part of the method stipulated by the disclosure.

Embodiments can be implemented in digital electronic circuitry, or in computer hardware, firmware, software, or in combinations thereof. A system or apparatus can be implemented in a computer program product tangibly embodied or stored in a machine-readable hardware storage device for execution by a programmable processor; and method actions can be performed by a programmable processor executing a program of instructions to perform operations by operating on input data and generating output. The techniques described herein can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable computers and processors include, by way of example, both general and special purpose microprocessors, or any other kind of central processing unit or controller. Generally, a processor (such as a central processing unit) will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as hardware storage devices, EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

REFERENCE SIGNS 1 trench
2 sample
3 cross-section
4 region of interest (ROI)
L length of trench
D depth of trench
W width of trench/cross-section
21 Step: Selecting region of interest
22 Step: Excavating initial trench
23 Step: Excavating trench
24 Step: Excavating cross-section
31 Step: Selecting region of interest
32 Step: Excavating trench
33 Step: Excavating cross-section
41 Step: Selecting region of interest
42 Step: Milling with medium ion dose
43 Step: Milling with low ion dose
44 Step: Milling with increasing ion dose
51 milling step for milling initial trench
52 milling step for milling trench
53 milling step for milling cross-section
54 position of region of interest (ROI)
55 profile of trench
56 cross-section (profile view)
57 slope of trench (profile view)
61 region to be milled for initial trench
62 region to be milled for trench 63 region to be milled for cross-section
64 region of interest (ROI)
65 scan direction
66 milling direction towards ROI (forward milling)
67 reversed milling direction (backward milling)
W width dimension of trench
L length dimension of trench
d distance: ROI—milling region
71 region to be milled for initial trench
72 region to be milled for trench
73 region to be milled for cross-section
74 region of interest (ROI)
75 scan direction
76 milling direction towards ROI (forward milling)
77 reversed milling direction (backward milling)
W width of trench
L length of trench
801 particle-beam apparatus
802 sample chamber
803 electron-optical column
804 electron source
805 first lens system
806 optical axis of electron-optical column
807 second lens system
808 aperture
809 deflection system
810 detector
811 controller unit
813 sample
814 sample holder
815 focusing lens
816 deflection system
817 optical axis of ion-optical column
818 ion-optical column
819 ion source
820 gas-injection mechanism

What is claimed is:

1. A method for preparing a cross-section at a position of a sample, the method comprising:
   a) excavating a trench having sidewalls by ion beam milling along a first path in a first milling direction which leads away from the position of the sample; and
   b) excavating the cross-section of the sample by changing the sidewalls of the trench and enlarging the trench by ion beam milling along a second path which overlaps with at least a portion of the first path in a second milling direction which is the reverse direction of the first milling direction and which leads toward the position of the sample, whereupon milling is completed at the position of the sample,
   wherein a largest milling depth is achieved at the completion of b).

2. The method of claim 1, further comprising, before a), excavating an initial trench by milling in the second milling direction.

3. The method of claim 2, wherein b) comprises applying an ion dose which increases with decreasing distance of the ion beam from the position of the sample.

4. The method of claim 2, wherein an ion dose is applied during a) which is different from an ion dose applied when excavating the initial trench.

5. The method of claim 4, wherein:
   excavating the initial trench comprises applying a first ion dose suitable for coarse removal of sample material; and
   the method further comprises
   applying a second ion dose suitable for removal of redeposited material during a); and
   applying an increasing ion dose until a full ion dose for a desired depth of the cross-section is applied when completing the milling of the cross-section during b).

6. The method of claim 5, wherein the first ion dose is higher than the second ion dose.

7. The method of claim 5, wherein the dose ratio of the first ion dose, the second ion dose and the full ion dose is ½:⅓:1.

8. The method of claim 2, wherein:
   a) comprises milling a first region;
   b) comprises milling a second region of the sample;
   excavating the initial trench comprises milling a third region of the sample;
   the first, second and third regions are defined by their sizes, positions and geometrical shapes; and
   the first region and the third region differ in size and/or position.

9. The method of claim 8, wherein the first region overlaps with the third region.

10. The method of claim 8, wherein the first region is larger than the third region.

11. The method of claim 8, wherein the third region is located a distance from the position of the sample.

12. The method of claim 1, wherein:
   a) comprises milling a first region of the sample;
   b) comprises milling a second region;
   the first and second regions are defined by their sizes, positions and geometrical shapes; and
   the first region and the second region differ in size and/or position.

13. The method of claim 12, wherein the first region is located a distance from the position of the sample.

14. The method of claim 12, wherein the first region overlaps with the second region.

15. The method of claim 12, wherein the first second and third regions have a tapered width.

16. The method of claim 15, wherein the first second and third regions are trapezoids.

17. The method of claim 1, wherein a) and/or b) comprises using gas assisted etching when excavating.

18. The method of claim 1, comprising using a FIB system during a) and b).

19. A computer program product residing on a non-transitory computer readable hardware storage device, the computer program product comprising instructions for causing a system to:
   a) excavate a trench having sidewalls by ion beam milling a sample along a first path in a first milling direction which leads away from a position of the sample where a cross-section of the sample is to be formed; and
   b) excavate the cross-section of the sample by changing the sidewalls of the trench and enlarging the trench by ion beam milling along a second path which overlaps with at least a portion of the first path in a second milling direction which is the reverse direction of the first milling direction and which leads toward the position of the sample, whereupon milling is completed at the position of the sample,
   wherein a largest milling depth is achieved at the completion of b).

20. The computer program product of claim 19, wherein the system comprises a FIB system.

21. The computer program product of claim 19, wherein the instructions are executable by a controller unit of the system.

22. The method of claim 1, wherein enlarging the trench during b) increases a depth of the trench.

23. The computer program product of claim 19, wherein enlarging the trench during b) increases a depth of the trench.

\* \* \* \* \*

UNITED STATES PATENT AND TRADEMARK OFFICE
CERTIFICATE OF CORRECTION

PATENT NO. : 9,947,507 B2
APPLICATION NO. : 14/795489
DATED : April 17, 2018
INVENTOR(S) : Lorenz Lechner Page 1 of 1

It is certified that error appears in the above-identified patent and that said Letters Patent is hereby corrected as shown below:

In the Specification

Column 9, Line 59, delete "62." insert -- 62, --;

Column 11, Line 31, delete "Galium" insert -- Gallium --;

In the Claims

Column 14, Line 37, Claim 15, after "first" insert -- , --;

Column 14, Line 39, Claim 16, after "first" insert -- , --.

Signed and Sealed this
Twenty-eighth Day of August, 2018

Andrei Iancu
*Director of the United States Patent and Trademark Office*